United States Patent [19]

Banas et al.

[11] 4,009,215

[45] Feb. 22, 1977

[54] PREPARATION OF $CCl_3F$ AND $CCl_2F_2$ FROM FLUORSPAR AND $CCl_4$

[76] Inventors: Edmund Odon Banas, Brackenville Road, R.D. No. 1, P.O. Box 327, Hockessin, Del. 19707; Wesley Gerald Schindel, Valley Court Apts., Apt. D-7, Pennsville, N.J. 08070

[22] Filed: Mar. 16, 1976

[21] Appl. No.: 667,372

[52] U.S. Cl. .............................. 260/653.8; 23/252 R
[51] Int. Cl.[2] .................. C07C 17/10; C07C 19/08
[58] Field of Search ................................ 260/653.8

[56] References Cited

UNITED STATES PATENTS

| 2,739,989 | 3/1956 | Barringer et al. | 260/653.8 |
| 3,686,338 | 8/1972 | Vecchio et al. | 260/653.8 |

*Primary Examiner*—D. Horwitz

[57] ABSTRACT

Preparation of $CCl_3F$ and $CCl_2F_2$ by countercurrently contacting $CaF_2$ and $CCl_4$ under reaction conditions to provide high conversion both of $CCl_4$ to fluorine-containing products and $CaF_2$ to $CaCl_2$.

5 Claims, 3 Drawing Figures

PREPARATION OF CCL$_3$F AND CCL$_2$F$_2$ FROM FLUORSPAR AND CCL$_4$

BACKGROUND OF THE INVENTION

The fluorocarbons CCl$_3$F and CCl$_2$F$_2$, designated in the nomenclature conventional to the field as fluorocarbons 11 and 12, respectively, are used in a wide variety of industrial applications. Mixtures of these products have conventionally been prepared by first reacting fluorspar, CaF$_2$, with sulfuric acid to produce calcium sulfate and hydrofluoric acid. The hydrofluoric acid so produced then was reacted with carbon tetrachloride under reaction conditions suitable to produce the desired mixture of fluorocarbons 11 and 12. In the interests of greater process efficiency, previous attempts have been made to directly react fluorspar with carbon tetrachloride. However, these previous attempts have met with limited success. The calcium fluoride has a marked tendency to agglomerate during the course of reaction. Moreover, the fluid bed systems frequently used in such reactions are characterized by a low gas retention time. This low gas retention time limits the conversion of CCl$_4$ and requires the recovery of large quantities of the reactants. While large excesses of either CCl$_4$ or fluorspar can cause substantially complete conversion of the other component, an efficient process for the direct reaction of these materials have previously not been available.

SUMMARY OF THE INVENTION

The present invention provides an improved process for the direct reaction of calcium fluoride and carbon tetrachloride to form fluorocarbons 11 and 12, characterized by a markedly greater conversion of both reactants to the desired products than has heretofore been realized.

Specifically, the present invention provides an improvement in the process of bringing into contact, under reaction conditions and at a temperature of about from 300° to 650° C, calcium fluoride and carbon tetrachloride to form a mixture of CCl$_3$F and CCl$_2$F$_2$, which improvement comprises contacting the reactants countercurrently in at least one reaction vessel with axial plug flow and radial shear mixing.

There is further provided an improved apparatus in which the instant process can be carried out, comprising a tubular reactor having a first and a second end, means for introducing solid reactant at the first end and removing it at the second end, means for introducing gaseous reactant at the second end and removing it at the first end, and means for rotating the reactor to provide radial shear mixing of the reactants with axial plug flow.

DETAILED DESCRIPTION OF THE INVENTION

Figure 1:
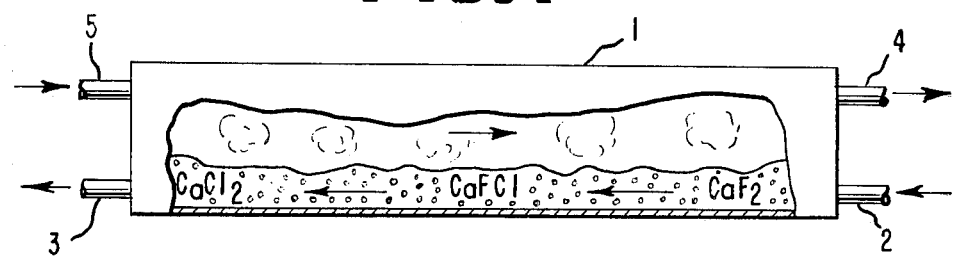
FIG. 1 is a cross sectional schematic view of a single reaction vessel which can be used in the process of the instant invention.

The calcium fluoride, or fluorspar, used in the instant process should generally have a small particle size. The desired particle size is preferably obtained, for example, by in situ grinding to particles of less than about 10 microns. Preferably, a particle size of less than about 2 microns is used, and sub-micron particles have been found to provide particularly good conversion of the carbon tetrachloride. Particularly desirable results are obtained when the fluorspar is purified to comprise at least about 97% CaF$_2$. However, less highly purified fluorspar can also be used in the present invention. Carbon tetrachloride of normal commercial purity can be used in the instant process with satisfactory results.

The two reactants are brought into contact at a temperature of about from 300° to 650° C. Generally, temperatures of about from 400° to 550° C are preferred, and temperatures of about from 480° to 550° C have been found to give particularly satisfactory results. The reactants are generally brought to these temperatures by conventional external heaters. The elevated temperatures can be maintained by the same means or by an exothermic reaction within the reactor itself. A particularly convenient way of effecting such an exothermic reaction is the inclusion in the carbon tetrachloride feed or a minor amount of an under-chlorinated product such as methylene chloride and methyl chloride in combination with chlorine gas. With such additional components in the reactant stream, the chlorine heats the reaction mixture by reaction with the under-chlorinated products and, at the same time, suppresses the decomposition of carbon tetrachloride to form undesirable two carbon by-products. In general, the quantity of chlorine gas comprising about from 10 to 15 weight percent of the carbon tetrachloride feed has been found effective for this purpose. The quantity of methylene chloride or methyl chloride is preferably such as to consume approximately three quarters of the chlorine gas in the complete chlorination of the under-chlorinated reactants.

The reactants are normally passed through the reaction vessel at varying rates, consistent with the different physical forms in which they are usually found. Accordingly, the carbon tetrachloride and attendant gaseous components are transported to provide a residence time within the reaction vessel of about from 10 seconds to 20 minutes. The solid fluorspar is removed to provide a residence contact time with the gaseous components of about from 30 minutes to 6 hours. Particularly satisfactory results have been obtained using a residence time of about from 1 to 2 minutes and about from 3 to 4 hours for the gaseous components and the fluorspar, respectively. It has been found that, in the preferred reaction vessels, residence time of less than about 30 minutes for the fluorspar can result in unsatisfactorily poor conversion, while residence times in excess of 6 hours do not bring about greater conversion of the components.

In accordance with the instant process, the reactants are brought into contact in a countercurrent plug flow. The term plug flow is used herein in its conventional sense, indicating that successive quantities of reactants flow through the apparatus in substantially the same order as they entered it, without axial turbulence or back-mixing.

Figure 2:
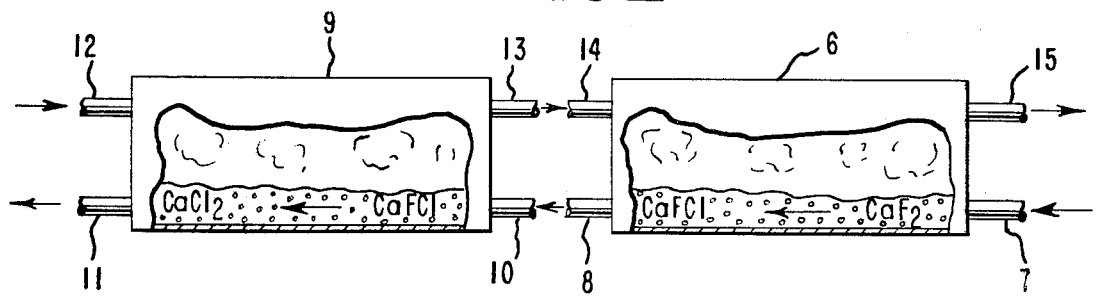
FIG. 2 is a cross sectional schematic view of a two vessel reaction system which can be used for the instant process.

A particularly satisfactory means for providing the required countercurrent flow is the use of a tubular reactor. Satisfactory tubular reactors are generally about from 0.3 to 4.6 meters in diameter and about from 1.5 to 50 meters in length. Such a reactor is schematically illustrated in FIG. 1, in which tubular reactor 1 is provided with solid reactant inlet 2 and solid reactant outlet 3 as well as gaseous reactant inlet 4 and gaseous reactant outlet 5. Calcium fluoride is introduced into the tubular reactant passing in the direction indicated, while gaseous carbon tetrachloride, optionally in combination with under chlorinated products and chlorine gas, is fed countercurrently to the fluorspar. As the fluorspar progresses along the length of the tubular reactor, it is first converted to CaFCl and finally to calcium chloride, after which it is removed from the reaction vessel. In a two stage reaction system, such as illustrated in FIG. 2, the calcium fluoride is introduced into first reactor 6 through inlet 7. The calcium fluoride is reacted with the gaseous components flowing countercurrently and, when substantially complete conversion to CaFCl has taken place, removed through solid reactant outlet 8. The CaFCl is introduced into second reactor 9 through solid reactant inlet 10. In this second reactor, conversion to calcium chloride is completed by contact with the gaseous components in the second reactor. After conversion to calcium chloride, the solid reactant is removed through the solid reactant outlet 11. The gaseous components flow countercurrently to the solid components. The carbon tetrachloride and associated gases are introduced first through gaseous inlet 12 and removed from the second reaction vessel through gaseous outlet 13. The partially converted gaseous reactants are then introduced into the first reaction vessel through inlet 14 and the desired products are removed through gaseous outlet 15.

In a two reactor system as described above, the requirement for countercurrent flow is satisfied if reactants are supplied to each reactor as specified. The actual flow within the individual reactors may therefore be cocurrent or countercurrent, as long as an overall countercurrent reactant flow is maintained for the system as a whole. Thus, carbon tetrachloride is brought into contact with partly chlorinated fluorspar in one reaction vessel, and the resulting partly fluorinated organic product is brought into contact with fresh fluorspar in the other reaction vessel. However, even in a two-reactor system, countercurrent flow within each reactor is preferred.

Figure 3:
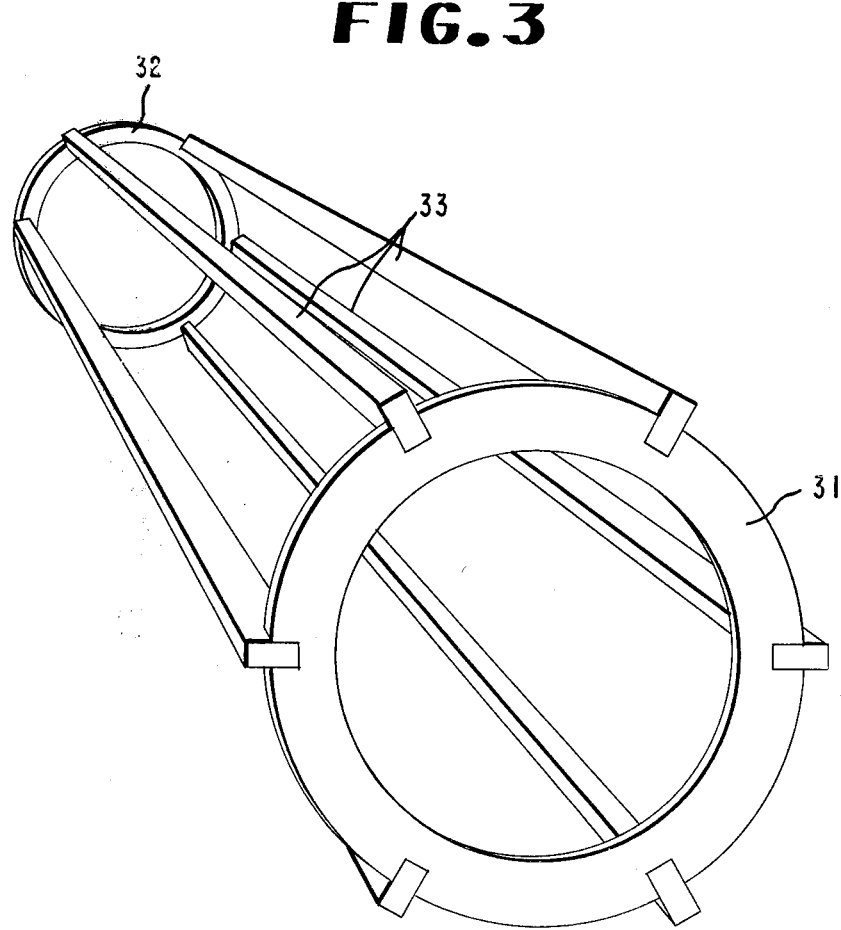
FIG. 3 is a perspective view of a mixing device for use in the apparatus of FIGS. 1 or 2.

In accordance with the instant invention, the components are subjected to radial shear mixing during the course of the reaction. Such mixing should provide radial turbulence of the components while not interrupting the axial plug flow. This mixing can be provided by a variety of methods, including, for example, internal mixers or rotation of the tubular reaction vessel with appropriate rotary fittings for the addition and removal of the reactants. Specific apparatus of this type is well known to those skilled in the art. A rotational rate to give a peripheral speed of about from 0.9M min.$^{-1}$ to 30M min.$^{-1}$ is satisfactory for most tubular reactors. In general, a peripheral speed of about 9M min.$^{-1}$ is preferred. In conjunction with such rotation, it is often desirable to provide internal devices to aid in the admixture of the components and the break up of any agglomerated solid reactant. A particularly satisfactory internal mixing device is shown in FIG. 3, which comprises an internal cylindrical cage for insertion in the tubular reactor. This representative device comprises supporting end elements 31 and 32, connected with longitudinal bars 33. This device has been found to rotate with the solid contents of a tubular reactor for at least part of its rotational cycle, and then drop to the bottom of the tubular reactor, breaking up agglomerated solid reactants. The longitudinal bars 33 provide a "wiping" action along the sides of the reactor, which facilitates the operation of the instant process to a greater extent than internal balls or cylinders. The required radial shear mixing can also be provided by driven rotation of the internal mixing device in addition to or in place of rotation of the reactor.

The solid components can be moved through the tubular reactor by any convenient means. The radial shear mixing can be used with the addition and removal of solid reactant at the two ends of the reactor. Preferably the reactor is maintained at an angle to facilitate flow of the solid reactant through the tubular reactor. While the angle used will, of course, depend on the desired rate of flow, angles varying from horizontal about 0.7 to 5.0 degrees have been found convenient.

The gaseous product stream recovered from the instant process is a mixture of fluorocarbons 11 and 12, unreacted carbon tetrachloride and various by-products including $C_2Cl_4$. These organic products can be separated by techniques well known to those skilled in the art. Continuous distillation has been found to be particularly satisfactory.

The instant process provides an economical method of preparing fluorocarbons 11 and 12, in that it reduces the need for recovery and recycling of the fluorspar with the gaseous components and the attendant difficult recovery of $CFCl_3$ from product streams highly diluted with carbon tetrachloride. The recycling of calcium fluorochloride was particularly cumbersome, involving reaction with water to form calcium fluoride and calcium chloride. The calcium fluoride precipitates and is reused after drying, while the calcium chloride remains in solution and is generally discarded.

The yields achieved are significantly greater than would be predicted, for example, from the pertinent teachings of Schiemann et al., in Zeitschrift fur Physikalische Chemie Neue Folge 38 56–59 (1963). Substantially complete utilization of both the $CCl_4$ and the fluorine values of the fluorspar can be obtained.

The present invention is illustrated in the following specific examples.

EXAMPLE 1 AND COMPARATIVE EXAMPLE A

Countercurrent flow and cocurrent flow were compared in experimental equipment which comprised two series-connected heated fixed bed reactors through which gaseous $CCl_4$ was passed. Cocurrent operation was simulated by directing the gas stream through the first reactor containing $CaF_2$ and thereafter through the second reactor containing CaFCl. Countercurrent operation of the present invention was simulated by passing the gas stream through the reactors in the opposite order.

CaFCl was prepared by fusing approximately equimolar amounts of $CaCl_2$ and $CaF_2$, mixing and thereafter grinding the cooled mixture. Analysis of the CaFCl thus prepared showed that the mixture contained a small amount of free $CaF_2$ corresponding to the hypothetical empirical formula $CaCl_{0.94}F_{1.06}$. The $CaF_2$ used was finely ground precipitated $CaF_2$.

Approximately equimolar amounts of $CaF_2$ and CaFCl were charged to the first and second cylindrical reactors, respectively. The temperature of the reactors was maintained at about 550° C.

In Comparative Example A, simulating cocurrent operation, $CCl_4$ was fed to the reactor containing $CaF_2$ by means of a calibrated motor-driven pump at the rate of about 1 mole per hour for each 0.41 moles of CaFCl and $CaF_2$. In order to provide smoother flow, 11–14 mol. percent based on $CCl_4$ of nitrogen was cofed.

The resultant residence times were insufficient to permit complete reaction. Preliminary experiments showed that fluorine-containing exit gases consisted of $CCl_3F$ and about 2 mole percent $CCl_2F_2$. After 3 hours, the reaction was stopped and the CaFCl and $CaF_2$ beds were analyzed for chloride ion. From the results, the conversion of $CCl_4$ predominantly to $CCl_3F$ was calculated.

Analysis of the upstream ($CaF_2$) reactor bed showed that about 65 mole percent of the fluorine of the bed had exchanged with the $CCl_4$. This degree of conversion of $CaF_2$ corresponds to the conversion of about 17.8 mole percent of the $CCl_4$ fed to produce predominantly $CCl_3F$. Analysis of the downstream bed showed that only 1.4 additional mole percent of $CCl_3F$ was formed on passage through the second bed.

The low degree of conversion in the CaFCl reactor demonstrates the Schiemann et al. conversion limit of $CCl_4$ to $CCl_3F$ of about 18% in the reaction of CaClF to form $CaCl_2$.

In Example 1, the procedures of Comparative Example A were repeated, except that the gas stream was directed first through the CaFCl reactor and thereafter through the $CaF_2$ reactor.

Analysis showed that the gas stream leaving the first reactor contained 9.3 mole percent $CCl_3F$ and the stream leaving the second reactor contained 24.3 mole percent $CCl_3F$. Increased conversion of $CCl_4$ to $CCl_3F$ and also of $CaF_2$ to $CaCl_2$ via CaFCl was therefore realized.

EXAMPLE 2

Operation in accordance with the present invention was simulated by charging 120 gm (1.54 mole) of finely ground fluorspar to a tubular reactor containing a loosely fitting grinder substantially of the type shown in FIG. 3. While the reactor, heated to 480° C, was rotated at a peripheral speed of about 9M min.$^{-1}$ about its longer axis, preheated $CCl_4$ vapors were fed to one end at the rate of 442.5 gm hr$^{-1}$ (2.88 mole hr$^{-1}$). Product gases, after about 2.1 minutes residence time, left the opposite end and, after neutralization, were analyzed by gas chromatography.

After 4 hours, the experiment was terminated. The results are shown in the Table. The rate of conversion of $CCl_4$ steadily decreased with time as reflected in the increasing proportion of $CCl_4$ and the decreasing proportion of $CCl_3F$ and $CCl_2F_2$ in the product stream. $C_2Cl_4$ and $C_2Cl_6$ result from pyrolytic decomposition of $CCl_4$.

The spent fluorspar was nonsticky, free-flowing powder. There was substantially no sticking on the walls of the reactor.

TABLE

| Elapsed Time (Hr.) | Analysis (Mole %) | | | | | [CFCl$_3$/CCl$_4$] | Conversion (Mole %) CaF$_2$ → CaCl$_2$ |
| --- | --- | --- | --- | --- | --- | --- | --- |
| | CCl$_4$ | CCl$_3$F | CCl$_2$F$_2$ | C$_2$Cl$_4$ | C$_2$Cl$_6$ | | |
| 0–0.5 | 45.8 | 34.2 | 12.6 | 7.1 | 0.2 | 0.75 | 25.9 |
| 0.5–1.0 | 55.9 | 31.3 | 4.8 | 7.7 | 0.2 | 0.56 | 43.8 |
| 1.0–2.0 | 66.9 | 21.5 | 2.1 | 9.1 | 0.3 | 0.32 | 65.8 |
| 2.0–3.0 | 77.6 | 11.8 | 0.6 | 9.6 | 0.4 | 0.15 | 76.9 |
| 3.0–4.0 | 81.6 | 8.1 | 0.2 | 9.5 | 0.5 | 0.10 | 84.1 |

If a continuous feed of fresh fluorspar were provided at the upstream end with removal of spent fluorspar at the downstream end of the reactor, a product mixture at steady state would result containing at least as high a proportion of $CCl_3F$ and $CCl_2F_2$ as under the 0–0.5 hr. condition of the Table accompanied by high fluorspar conversions.

We claim:

1. In the process of bringing into contact, under reaction conditions and at a temperature of about from 300° to 650° C, calcium fluoride and carbon tetrachloride to form a mixture of $CCl_3F$ and $CCl_2F_2$, the improvement which comprises contacting the reactants countercurrently in at least on reaction vessel with axial plug flow and radial shear mixing.

2. A process of claim 1 wherein the calcium fluoride has a particle size, on contact with the carbon tetrachloride, of less than about 10 microns.

3. A process of claim 1 wherein the reactants are mixed by rotation of the reaction vessel.

4. A process of claim 1 wherein the reaction mixture further comprises chlorine gas and at least one compound selected from the group consisting of methylene chloride and methyl chloride.

5. A process of claim 1 wherein the reactants are brought into contact in a single tubular reaction vessel.

* * * * *